US011823794B2

(12) United States Patent
Pronk et al.

(10) Patent No.: US 11,823,794 B2
(45) Date of Patent: Nov. 21, 2023

(54) METHOD TO ANALYZE LOG PATTERNS

(71) Applicant: KONINKLIJKE PHILIPS N.V., Eindhoven (NL)

(72) Inventors: Serverius Petrus Paulus Pronk, Vught (NL); Johannes Henricus Maria Korst, Eindhoven (NL); Mauro Barbieri, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 532 days.

(21) Appl. No.: 15/734,298

(22) PCT Filed: Jun. 13, 2019

(86) PCT No.: PCT/EP2019/065421
§ 371 (c)(1),
(2) Date: Dec. 2, 2020

(87) PCT Pub. No.: WO2019/243145
PCT Pub. Date: Dec. 26, 2019

(65) Prior Publication Data
US 2021/0225500 A1   Jul. 22, 2021

Related U.S. Application Data

(60) Provisional application No. 62/687,369, filed on Jun. 20, 2018.

(51) Int. Cl.
*G06F 11/07* (2006.01)
*G16H 40/40* (2018.01)
*G16H 40/63* (2018.01)

(52) U.S. Cl.
CPC .......... *G16H 40/40* (2018.01); *G06F 11/079* (2013.01); *G06F 11/0775* (2013.01); *G06F 11/0787* (2013.01); *G16H 40/63* (2018.01)

(58) Field of Classification Search
CPC ............ G06F 11/0775; G06F 11/0787; G06F 11/079; G16H 40/40
See application file for complete search history.

(56) References Cited

U.S. PATENT DOCUMENTS 9,405,755 B1  8/2016  Bailey
9,665,420 B2  5/2017  Jilani
(Continued)

FOREIGN PATENT DOCUMENTS

JP   2016024786       2/2016
JP   2016192064 A    11/2016

OTHER PUBLICATIONS

International Search Report and Written Opinion dated Oct. 8, 2019 For International Application No. PCT/EP2019/065421 filed Jun. 13, 2019.

*Primary Examiner* — Nadeem Iqbal

(57) ABSTRACT

Analysis of a log pattern for use in diagnosing a medical imaging device operates on log data including log events and service calls, each associated with a subset of log events within a service call time frame of a call time of the service call. Preprocessing (64) generates normalized log events (66) by removing or replacing content of the log events and linking each normalized log event with one or more service calls. Pre-analysis (68) identifies a test set of normalized log events that match a log pattern (40) and a test set of service calls (42) linked with the test set of normalized log events. The test set of service calls is analyzed (74) to identify hit service calls (46) each belonging to the test set of service calls and for which the log pattern under analysis has a hit.

20 Claims, 3 Drawing Sheets

(56) References Cited

U.S. PATENT DOCUMENTS

| | | | |
|---|---|---|---|
| 10,514,974 B2 * | 12/2019 | Togawa | ............... G06F 11/079 |
| 2004/0199828 A1 * | 10/2004 | Cabezas | ............... G06F 11/079 |
| | | | 714/39 |
| 2006/0184529 A1 | 8/2006 | Berg | |
| 2008/0059120 A1 | 3/2008 | Xiao | |
| 2012/0179646 A1 | 7/2012 | Hinton | |
| 2015/0220605 A1 | 8/2015 | Syed | |
| 2016/0124823 A1 | 5/2016 | Ruan | |
| 2017/0180404 A1 | 6/2017 | Bersch | |
| 2017/0293542 A1 | 10/2017 | Xu | |

* cited by examiner

METHOD TO ANALYZE LOG PATTERNS

CROSS REFERENCE TO RELATED APPLICATIONS

This application is the U.S. National Phase application under 35 U.S.C. § 371 of International Application No. PCT/EP2019/065421 filed Jun. 13, 2019, which claims the benefit of U.S. Provisional Patent Application No. 62/687,369 filed Jun. 20, 2018. These applications are hereby incorporated by reference herein.

FIELD

The following relates generally to the medical imaging device servicing arts, fault diagnosis arts, log pattern detection arts, and related arts.

BACKGROUND

Medical imaging systems such as magnetic resonance imaging (MRI), transmission computed tomography (CT), and intraoperative X-ray (iXR) scanners occasionally experience a system failure that can in some cases be resolved by a remote service engineer (RSE). Quite often, however, a field service engineer (FSE) has to visit the hospital to resolve the issue. Especially when a part has to be replaced, it is unavoidable that an FSE visits the hospital. Depending on whether the root cause of a system failure can be determined remotely, resolving the issue may require multiple FSE visits when the required part is not available during the first visit. In the first visit, the FSE determines the root cause of the problem and determines whether one or more parts have to be replaced to resolve the issue, and if so, which part(s). After ordering the part(s), the FSE will do the actual replacement in a second visit. Incidentally, the identification of the root cause is difficult and more than two visits may be needed to resolve the issue if the root cause cannot be unambiguously determined in the first visit.

To reduce the unplanned downtime of medical imaging systems due to these failures and to reduce the associated maintenance costs, it would be advantageous to increase the fraction of issues that can be resolved remotely; and, for those issues where an FSE needs to visit the hospital, to decrease the number of visits that are needed to resolve the issue. The number of visits can be decreased by diagnosing the issue remotely.

To remotely determine the most probable root cause of a failure, machine log data can be used. When in operation, many commercial medical imaging systems continuously produce logging data. These are timestamped messages containing status information, information about events, as well as warning and error content. Typically, this logging data is stored locally, so that an FSE can inspect the data when on site. Additionally, a service engineer with appropriate access authorization may be able to remotely inspect the logging data. Furthermore, in some installations, logging data is uploaded (e.g. on a daily basis) to a central storage server, where it can be analyzed to identify the most common issues for the complete installed base of imaging systems.

To aid in the root cause analysis of system failures, one approach is to create log patterns that correlate with known failure modes. Based on experience and reviews of log event data, a log pattern can be handcrafted by making logical combinations of the occurrence or non-occurrence of certain log events within a given time span, together with a cause-solution tree, which lists a number of possible causes of the failure, together with one or more solutions per cause. Upon a service call from a hospital due to a system failure, the log patterns are applied to the log events generated over some time interval prior to the call, e.g., during one day or one week prior to the call. If a log pattern occurs one or more times, an alert is generated so that an engineer can use it in the root cause analysis. A log pattern has a hit in a sequence of log events that have been generated by one machine in a given interval of time if there is a time interval, the length of which is equal to the time span of the log pattern, in which the Boolean expression of the log pattern evaluates to true. Once a hit has been found, the time interval identified is shrunk maximally to just 'contain' the hit, which is then counted as one hit, and searching for additional hits is continued by repositioning the window directly after the shrunken interval. A log pattern may also be said to have a hit for a service call, by which it is meant that the log pattern has at least one hit in a predefined interval of time prior to this service call.

Analysis of the performance of a log pattern can be quantified in various ways, such as: How often does it occur and, when it occurs, does it occur at the right occasion, i.e., does it relate to the failure at hand, does the cause-solution tree provide useful guidance, et cetera. Log patterns that generate too many alerts can have a detrimental effect on the effectiveness of the root cause analysis; while log patterns that produce too few alerts are of limited diagnostic value. This performance analysis is typically done on historical data.

The following discloses certain improvements.

SUMMARY

In some embodiments disclosed herein, a non-transitory storage medium stores configuration data including at least a service call time frame and normalization rules for removing or replacing content, and instructions readable and executable by an electronic processor to perform a log pattern analysis method operating on medical imaging device log data including log events and further including service calls each having a call time wherein each service call is associated with a subset of log events occurring within the service call time frame of the call time of the service call. The log pattern analysis method comprises: performing preprocessing of the medical imaging device log data including generating normalized log events by removing or replacing content of the log events according to the normalization rules and linking each normalized log event with one or more service calls having associated log events matching the normalized log event; performing pre-analysis including identifying a test set of normalized log events that match a log pattern under analysis and a test set of service calls linked with the test set of normalized log events; analyzing the test set of service calls to identify hit service calls wherein each hit service call belongs to the test set of service calls and for which the log pattern under analysis has a hit; and controlling a display to present a log pattern report summarizing the hit service calls.

In some embodiments disclosed herein, a medical imaging device diagnosis system includes a non-transitory storage medium as set forth in the immediately preceding paragraph, a server computer operatively connected with the non-transitory storage medium to read and execute the instructions to perform the log pattern analysis method, and a diagnostic design computer operatively connected with the non-transitory storage medium to read and execute the instructions to perform a log pattern editing method. The system may further include a field service engineer computer operatively connected with the non-transitory storage medium to read and execute the instructions to perform a diagnostic assistance method.

In some embodiments disclosed herein, a log pattern analysis device comprises an electronic processor and a non-transitory storage medium storing instructions readable and executable by the electronic processor to perform a log pattern analysis method operating on medical imaging device log data including log events and further including service calls each having a call time wherein each service call is associated with a subset of log events occurring within a service call time frame of the call time of the service call. The log pattern analysis method comprises: performing preprocessing of the medical imaging device log data including generating normalized log events by removing or replacing content of the log events and linking each normalized log event with one or more service calls having associated log events matching the normalized log event; performing pre-analysis including identifying a test set of normalized log events that match a log pattern under analysis and a test set of service calls linked with the test set of normalized log events; and analyzing the test set of service calls to identify hit service calls wherein each hit service call belongs to the test set of service calls and the log pattern under analysis has a hit for each hit service call.

In some embodiments disclosed herein, a log pattern analysis method operates on medical imaging device log data including log events and further including service calls each having a call time wherein each service call is associated with a subset of log events occurring within a service call time frame of the call time of the service call. The log pattern analysis method comprises: removing or replacing content of the log events of the medical imaging device log data to generate normalized log events and linking each normalized log event with one or more service calls having associated log events matching the normalized log event; identifying a test set of normalized log events that match a log pattern under analysis and a test set of service calls linked with the test set of normalized log events; and analyzing the test set of service calls to identify hit service calls wherein each hit service call belongs to the test set of service calls and the log pattern under analysis has a hit for each hit service call. The log pattern analysis method is suitably performed by an electronic processor.

One advantage resides in providing a medical imaging device log pattern editor with automated performance analysis having high computational efficiency.

Another advantage resides in providing a medical imaging device log pattern editor with automated performance analysis having faster computational speed.

Another advantage resides in providing a medical imaging device log pattern editor that imposes reduced log data transfer traffic on an associated electronic data network.

Another advantage resides in providing a medical imaging device diagnostic system with improved diagnostic accuracy achieved by deployed log patterns having undergone more efficient performance analysis using a log pattern analyzer as disclosed herein.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
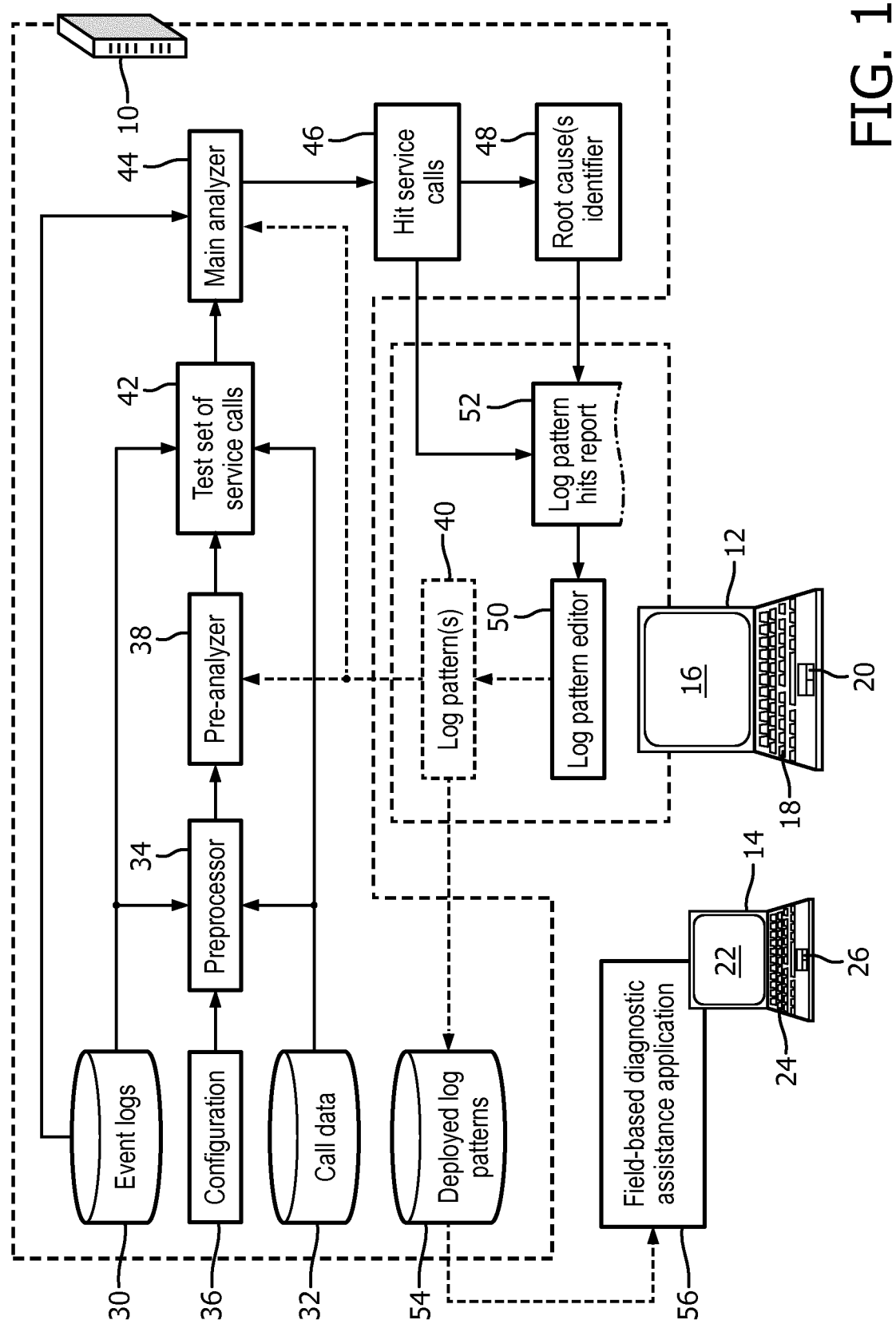
FIG. 1 diagrammatically illustrates a medical imaging system diagnostic system including a log pattern editing device with efficient automated performance analysis as disclosed herein, and a computerized diagnostic assistance device employing log patterns generated using the log pattern editing device.

The assessment of the performance of a log pattern using historical data entails applying the log pattern to log event data generated over many prior calls. Consider, for example, an installed base of thousands of medical imaging systems, which collectively experience 10,000 service calls per year. Suppose a log pattern hits for a 100 service calls per year, i.e., for 1% of all service calls. Making an assessment of the performance of the log pattern would require a significant number of service calls to be analyzed. Even analyzing log events for 1,000 random service calls (10% of all service calls) would only yield 10 service calls on average for which the log pattern would hit. This is generally not sufficient to do a proper statistical analysis, making this approach difficult or even infeasible in practice. On the other hand, processing all log events for all 10,000 service calls would yield 100 service calls for which the log pattern would hit. This would likely be sufficient for statistical analysis—however, the computing resources required to process this huge quantity of log events data would be very substantial, again making this approach difficult or even infeasible in practice.

In approaches disclosed herein, these difficulties are reduced by way of performing disclosed preprocessing of the historical log events data. This can be done once for a given time frame in the past (and optionally with certain other specified constraints) to generate a set of normalized log events that then undergo a disclosed pre-analysis to identify a superset of the service calls for which a given pattern hits. The preprocessing is not specific for a given log pattern (although in some embodiments known constraints on the type of log pattern to be analyzed may enable more effective normalization; this may be balanced against the goal of reusability of the normalized log data in selecting the extent of normalization). Due to the lack of log pattern specificity of the preprocessing, if a diagnostic designer is in the process of defining a new log pattern, then the log pattern may be adjusted and rerun against the same normalized log data generated once by the preprocessing, so that the preprocessing step need not be repeated. This facilitates rapid analysis of variations of the log pattern of the type likely to be generated by a diagnostic designer adjusting the log pattern in an effort to optimize it for a specific diagnostic task. The pre-analysis does depend on the log pattern, but operates on a reduced data set, i.e. the normalized data generated by the preprocessing, and hence is more efficient than analyzing all available log data. The pre-analysis can be seen as a filtering step that, for each log pattern, filters the set of all calls in a given time frame to a relatively small superset of calls for which the log pattern may hit.

The superset is chosen by the pre-analysis so as to ensure that no (or at least very few) hits with the log pattern under analysis are discarded. This is done by identifying the test set of normalized log events that match the log pattern under analysis. This matching is similar to conventional matching of (unnormalized) log events to the log pattern, except that matching of normalized content of the log events is handled differently. Conceptually, the log pattern may be viewed as being normalized, insofar as log pattern items that correspond to normalized fields of the log events are handled in accord with predefined normalized content matching rules for the defined normalization (these are said to be normalized log pattern items). In this context, a normalized log event is said to match the normalized log pattern under analysis if the normalized log event matches an individual, normalized log pattern item of the normalized log pattern. This may lead to some hits being in error (as compared with whether the unnormalized log event would hit the unnormalized log pattern); but, in no case (or at least in very few, unusual cases) will log events that actually hit the log pattern under analysis be erroneously discarded by the matching of the normalized log events with the normalized log pattern. Thus, the resulting test set is a superset in the sense that it includes all calls (or at least almost all calls) for which the log pattern under analysis has a hit, and also may (indeed usually will) include additional calls for which the log pattern under analysis does not have a hit.

With reference to FIG. 1, a medical imaging system diagnostic system is diagrammatically illustrated, which includes a log pattern editing device 10, 12 with efficient automated performance analysis as disclosed herein, and a computerized diagnostic assistance device 14 employing log patterns generated using the log pattern editing device. The log pattern editing device comprises a server computer 10 operatively connected with a non-transitory storage medium (not shown) to read and execute the instructions to perform a log pattern analysis method employing preprocessing and pre-analysis as disclosed herein, and a diagnostic design computer 12 operatively connected with the non-transitory storage medium to read and execute instructions to perform the log pattern editing method. The illustrative computerized diagnostic assistance device 14 is designated as a field service engineer computer 14 operatively connected with the non-transitory storage medium to read and execute the instructions to perform a diagnostic assistance method employing the log patterns deployed from the log pattern editing device 10, 12. In the foregoing, it will be appreciated that each of the electronic processors 10, 12, 14 may be embodied by a computer, server, desktop computer, notebook computer, or other microprocessor-based electronic processing device. Typically, the log pattern analysis method is performed by an electronic processor with high computational capacity, such as the illustrative server 10, due to the extensive computations involved in these analyses (which still remains relatively extensive even with the improved computational efficiency achieved by way of the preprocessing and pre-analysis as disclosed herein). The non-transitory storage media referred to herein may be variously embodied, e.g. as a hard disk drive, RAID array, or other magnetic storage medium, a solid state drive (SSD) or other electronic storage medium, an optical disk or other optical storage medium, various combinations thereof, and/or so forth. Further, it will be appreciated that the disclosed electronic processors may be variously combined, and/or the various non-transitory storage media may be variously combined, by way of electronic data networks or the like. For example, the log pattern editing device 10 may be implemented as a cloud computing resource comprising an ad hoc combination of a number of server computers.

Moreover, the computer or other electronic processor 12 that performs the log pattern editing method includes suitable user interfacing hardware to enable user interaction to perform the log pattern editing and review of the log pattern analysis results. By way of non-limiting example, the illustrative diagnostic design computer 12 which is programmed to perform the log pattern editing method (including invoking the log pattern analysis method performed by the server computer 10 to analyze the initial and/or edited log pattern) includes user interfacing hardware such as an illustrative display 16 (providing display of analysis results and optionally also including a touch sensitive overlay to serve as a user input device), keyboard 18, mouse, trackball, illustrative trackpad or other pointing device 20, and/or so forth. Likewise, the illustrative field service engineer computer 14 includes user interfacing hardware such as an illustrative display 22 (providing display of analysis results and optionally also including a touch sensitive overlay to serve as a user input device), keyboard 24, mouse, trackball, illustrative trackpad or other pointing device 26, and/or so forth.

The log pattern analysis operates on medical imaging device log data including log events and further including service calls. In illustrative FIG. 1, the log events are stored in a log events database 30, and data on the service calls is stored in a service calls database 32. This reflects a common data entry paradigm in which the log events are generated automatically and logged to the log events database 30 by the medical imaging device, while the service calls data are entered manually or semi-manually by a service engineer or other personnel and stored in the service calls database 32. However, this is merely illustrative, and it is contemplated to employ an integrated database that stores both log events and service call data. By way of non-limiting illustration, a medical imaging device may, for example, be a computed tomography (CT) imaging scanner, a magnetic resonance imaging (MRI) scanner, an image-guided therapy (iGT) device employing a C-arm X-ray or other imaging component, a positron emission tomography (PET) scanner, a gamma camera such as are used for single photon emission computed tomography (SPECT) imaging, hybrid imaging systems (e.g. PET/CT), or so forth.

Each service call has a call time, typically designated as a logged day/time when the customer called in the problem that led to a service call being opened. The call time may be designated variously, e.g. as the time a service call center agent manually entered the call time, or as an automatically generated timestamp for receipt of a customer call, or so forth. Each service call is associated with a subset of log events occurring within a service call time frame of the call time of the service call. The service call time frame is a configuration parameter of the log pattern analysis, and the service call time frame is preferably set to be of sufficient length that the subset of log events contains all log events that credibly could be causal to or correlative with the root problem that led to the service call. On the other hand, if the service call time frame is too long, then the subset of log events associated with the service call can become impractically large. An appropriate value for the service call time frame could be dependent on numerous factors, e.g. the country or region in which the medical imaging system is based and/or customer type (e.g., larger medical facilities may typically spend more time attempting in-house remediation of a problem whereas smaller medical facilities may resort to calling the vendor more quickly) or so forth.

Typically, the service call time frame extends strictly prior to (and usually up to) the call time of the service call, e.g. if the call time is exactly noon on February 20$^{th}$ and the length of the service call time frame is 24 hours then the subset of log events associated with the service call are those log events timestamped between noon February 19$^{th}$ and noon February 20$^{th}$ (the latter again being the call time). This approach assumes that by the time the service call is placed (i.e. the call time) the root cause should be evident from logs timestamped up to the call time. Using a strictly prior time frame also accommodates the common situation in which the medical imaging device may be taken offline upon detection of certain types of problems (and hence no longer be generating log events). However, it is alternatively contemplated for the service call time frame to additionally extend some length after the call time, e.g. with the call time being noon on February 20$^{th}$ and the length of the service call time frame being 24 hours, the subset of log events associated with the service call could be those log events timestamped between 2 pm February 19$^{th}$ and 2 pm February 20$^{th}$ (in this example extending two hours past the call time).

The disclosed preprocessing is diagrammatically indicated in FIG. 1 by a preprocessor 34, e.g. implemented by the server computer 10 programmed to perform preprocessing of the medical imaging device log data including generating normalized log events by removing or replacing content of the log events according to the normalization rules and linking each normalized log event with one or more service calls having associated log events matching the normalized log event. More generally, the preprocessing of the medical imaging device log data includes generating normalized log events by removing or replacing content of the log events and linking each normalized log event with one or more service calls having associated log events matching the normalized log event. In a suitable approach, the normalized content comprises standardized content that replaces data fields or other selected content of medical imaging device log entries that has variability amongst the log entries. In some specific implementations, the normalized content for a certain type of replacement may be null content, e.g. an empty string—such a normalization amounts to removing the content from the log event.

In one approach, a medical imaging device log event is normalized by replacing content of the medical imaging device log event with normalized content as defined by configuration data 36. For example, the configuration data 36 may suitably include normalization rules that define which fields of a log event are to be normalized and the standardized content with which to replace the content of these fields. Since the normalization amounts to replacing or removing information from the log event, two or more (or indeed many) different medical imaging device log events may normalize in this way to the same normalized medical imaging device log event. All medical imaging device log events that normalize to a particular normalized medical imaging device log event are said to "match" that particular normalized medical imaging device log event. Said another way, a medical imaging device log event is said to match a normalized medical imaging device log event if the medical imaging device log event, when normalized by replacing content with normalized content as defined by the configuration data 36, results in said normalized medical imaging device log event.

The goal of log pattern analysis is to assess how well the log pattern under analysis identifies service calls having a certain root cause (or set of root causes, e.g. somehow related). Thus, each normalized log event is linked with one or more service calls having associated log events matching the normalized log event. In one processing approach, log events associated with service calls (i.e. being part of subsets associated with service calls) are normalized while still being linked with their respective service call(s); then, identical (i.e. duplicative) normalized log events are merged to a single normalized log event that is linked to all service calls whose log events were involved in the merger. It will be appreciated that this "de-duplication" process results in the set of normalized log events being substantially smaller than the set of log events from which the set of normalized log events was derived. Furthermore, the normalized log events contain less information and hence can be processed more efficiently.

As diagrammatically indicated in FIG. 1, the preprocessor 34 does not rely upon any log pattern in performing the preprocessing to generate the normalized log events. However, it will be appreciated that the configuration 36 may be chosen to limit the removal or replacement (i.e. normalization) of data of the log events upon which the log pattern under analysis relies. A tradeoff can be made, wherein the data to be normalized is chosen to be sufficient to provide substantial computational efficiency improvement while retaining sufficient data to provide meaningful pre-analysis respective to a log pattern. The configuration data 36 may be stored in various ways depending upon the desired modification flexibility. For example, configuration data that is never expected to be changed may be hard-coded into the executable instructions implementing the log pattern analysis method. Configuration data that is expected to be rarely changed may be stored in a global configuration file that is only editable by certain authorized personnel (e.g. a lead diagnostic designer having responsibility for maintaining the log patterns analysis system). A local configuration file or task-specific configuration file may be used to store configuration data that is expected to be updated frequently, e.g. depending upon factors such as the particular type of log pattern under analysis and/or the particular set of historical log data being employed for the analysis (e.g., historical log data appropriate for a specific anticipated deployment context may be used, for example if the log pattern is being developed to diagnose a problem likely to occur in a pediatrics department then historical log data obtained from pediatrics departments may be used; whereas, if the log pattern is being developed to diagnose a problem likely to occur in a cardiology department then historical log data obtained from cardiology departments may be used; and/or so forth). It is noted that any change to the normalization rules applied by the preprocessor 34 will require the preprocessing using those normalization rules to be repeated, which is computationally relatively expensive.

The disclosed pre-analysis is diagrammatically indicated in FIG. 1 by a pre-analyzer 38, e.g. implemented by the server computer 10 programmed to perform pre-analysis including identifying a test set of normalized log events that match a log pattern 40 which is under analysis and a test set of service calls 42 linked with the test set of normalized log events. Again, as the goal of log pattern analysis is to assess how well the log pattern 40 under analysis identifies service calls having a certain root cause (or set of root causes, e.g. somehow related), the output of the pre-analyzer 38 is the test set of service calls 42 (rather than the intermediate test set of normalized log events that match the log pattern 40).

More particularly, the goal is to generate the test set of service calls 42 which is a superset of all service calls in the database that are hits for the log pattern 40 under analysis.

In other words, the test set of service calls 42 should include all service calls that are associated with subsets of log events that match the log pattern 40 under analysis (without missing any hits), but may also include additional service calls that do not match the log pattern 40 under analysis. To accomplish this, the pre-analysis identifies the test set of normalized log events that match the log pattern 40 under analysis using overinclusive matching in which the normalized log events (that is, the normalized content) is matched to corresponding normalized log pattern items using predefined normalized content matching rules.

The test set of service calls 42 serves as input to the main log pattern analyzer 44. Conventionally, the main log pattern analyzer 44 would be the only log pattern analysis, and would retrieve from the event logs database 30 all log events that are associated with all service calls in the service calls database 32. That is, the main analyzer 44 would conventionally process all log events that lie within the service call time frame of any service call contained in the calls database 32. This could be an enormous amount of data to process, making the main analysis computationally inefficient. By contrast, the log pattern analysis method of FIG. 1 leverages the preprocessor 34 and pre-analyzer 38 to reduce the number of relevant calls to the test set of service calls 42, which is greatly reduced compared with the total number of service calls in the database 32; yet, due to the overinclusiveness of the pre-analysis performed by the pre-analyzer 38 it is ensured that this test set of service calls 42 includes every service call for which the log pattern 40 under analysis scores a hit (and additionally includes some other service calls for which the log pattern 40 under analysis will not hit). The main log pattern analysis performed by the main log pattern analyzer 44 is thus made much more efficient by the "pre-filtering" of service calls performed by the preprocessor 34 and pre-analyzer 38, and more efficiently produces the set of service calls 46 that the log pattern 40 under analysis.

The main log pattern analyzer 44 is suitably implemented by the server computer 10 programmed to analyze the test set of service calls 42 to identify the hit service calls 46, where each hit service call belongs to the test set of service calls 42 and for which the log pattern 40 under analysis has a hit. It is noted that the main log pattern analyzer 44 operates on the "original" log events data from the database 30. That is to say, the main log pattern analyzer 44 does not operate on the normalized log events. Thus, there is no ambiguity in whether the log pattern 40 hits, because there is no information lost due to normalization. The effect of the main analyzer 44 is thus to take as input the overinclusive test set of service calls 42 and remove those service calls that do not actually hit the log pattern 40 so as to output the hit service calls 46.

The medical imaging device log data used in the log pattern analysis is historical data, that is, the service calls are all resolved service calls in which a root cause (or root causes) of the problem that triggered the service call have been identified. Thus, the root cause(s) of the service calls in the database 32 are known and stored as data for the service calls. Hence, a root causes identifier 48 is suitably implemented by the server computer 10 programmed to identify one or more root causes determined by the hit service calls 46. Said another way, the identified root cause(s) are the root causes that were entered into the service calls database 32 for the hit service calls 46 (e.g., by a field service engineer or other professional who responded to the service call and resolved the problem with the medical imaging device).

With continuing reference to FIG. 1, the log patterns analysis method implemented by the server computer 10 is, in a typical practical implementation, invoked by a diagnostic designer who operates the diagnostic design computer 12 to input the log pattern 40 using a log pattern editor 50, i.e. a user interface via which the log pattern 40 under analysis can be edited and the log pattern analysis method can be invoked to present a log pattern hits report 52 summarizing the hit service calls 46 for the edited log pattern 40 under analysis. For example, the log pattern report 52 may be displayed on the display 16 of the diagnostic design computer 12.

The summary of the hit service calls 46 may, by way of non-limiting illustrative example, include information on the identified one or more root causes 48, display of the "raw log event data", that is, the log events on which the log pattern 40 hit (optionally with some contextual surrounding log data, e.g. if the log pattern hit was on a set of log events spanning some time interval then the displayed context may include any additional log events that did not contribute to the hit but are timestamped at times between log events that did contribute to the hit, further optionally including context for some lead-in time interval before the first log event contributing to the hit and/or some lead-out time interval after the last log event contributing to the hit), and/or so forth. If the hit service calls 46 yielded a large number of different root causes 48 then the presented information on the identified root causes 48 may comprise a truncated list of the top-N root causes occurring most frequently amongst the hit service calls 46 along with a count of the number of hit service calls identifying each root cause. The displayed information may further include some quantification of the hit service calls 46, such as a count of the hit service calls (that is, the number of service calls on which the log pattern 40 under analysis hits), a ratio of the count of the hit service calls to a count of service calls in the medical imaging device log data, both the count and the ratio, or so forth. The foregoing are merely illustrative report content, and more generally the log pattern report 52 may include additional and/or other information such as the type(s) of medical imaging devices to which the hit service calls 46 pertain, the type(s) of imaging tasks those devices were being used for, and/or so forth.

It will be appreciated that the log pattern editing and analysis process can be repeated iteratively under guidance of the diagnostic designer operating the diagnostic design computer 12 to input the initial log pattern 40 via log pattern editing user interface 50, followed by invocation of the log patterns analysis method implemented by the server computer 10 to generate the log pattern report. After reviewing this report, the diagnostic designer may further edit the log pattern 40 via the log pattern editor 50 and invoke the log patterns analysis method to generate an updated log pattern report for the updated (i.e. further edited) log pattern, and so forth until the diagnostic designer is satisfied that the log pattern is producing optimized (or at least acceptable) diagnostic results, e.g. as quantified by sufficiently strong correlation with one or a few root causes, a manageable number of total hits, a sufficiently low rate of false positives (i.e. hit service calls that do not identify the root cause(s) that the log pattern is intended to diagnose), and/or so forth. In performing this iterative process under guidance of the diagnostic designer, the same normalized log data generated by the preprocessor 34 can be used for each iteration (this is because the preprocessing is not log pattern-specific). Hence, the computationally intensive preprocessing can be performed before the diagnostic designer begins log pattern editing via the log pattern editing user interface 50, and the editing is thus a fast process. More generally, the preprocessing can be done at a certain time t, and, as of time t, all diagnostic designers can start to use the log pattern analysis tool to compose a multitude of patterns in an interactive setting. At a certain time, e.g., after one year, this preprocessing may be redone to update the set of calls considered, e.g., to include more recent calls, and the diagnostic designers may start using the updated data as soon as this preprocessing is finished.

When the diagnostic designer is satisfied with the log pattern, then the user interface presented by the log pattern editing method (e.g. the log pattern editor user interface 50) may suitably provide a "save as" user dialog or the like via which the (final) edited log pattern 40 under analysis can be stored as a deployed log pattern in a deployed log patterns database 54, preferably annotated with one or more root causes determined by the hit service calls 46 in the final analysis run on the final edited log pattern 40. The deployed log pattern is thus designed to be diagnostic for the annotated one or more root causes. In practice, there may be further validation layers interposed between the finally optimized log pattern output by the log pattern editor 50 and actual deployment of that log pattern in the field. For example, the final log pattern may be reviewed by a lead diagnostic designer or otherwise may need to pass some approval process. In daily practice, a remote service engineer may take the output of the log pattern into account in a more detailed assessment of the issue, for example by performing additional tests. For example, more than one log pattern may give hits, providing inconclusive evidence that is then resolved by performing additional tests.

With continuing reference to FIG. 1, the deployed log patterns stored in the database 54 are applied during current service calls performed in the field. The computerized diagnostic assistance device 14 (illustrative field service engineer computer 14) is operatively connected with a non-transitory storage medium (not shown) to read and execute the instructions to perform a diagnostic assistance method (e.g., implemented as an illustrated field-based diagnostic assistance application program 56 running on the computer 14) including: applying a deployed log pattern to medical imaging device log data generated by a medical imaging device-under-service; and, conditional upon the deployed log pattern having at least one match in the medical imaging device log data generated by a medical imaging device-under-service, controlling the display 22 of the field service engineer computer 14 to present the one or more root causes annotated to the deployed log pattern in the database 54. The application program 56 may also present further information, such as displaying the log events that contributed to the log pattern match (again, optionally displayed in context including surrounding log events timestamped between or leading into and/or out of the log events making up the match).

Figure 2:
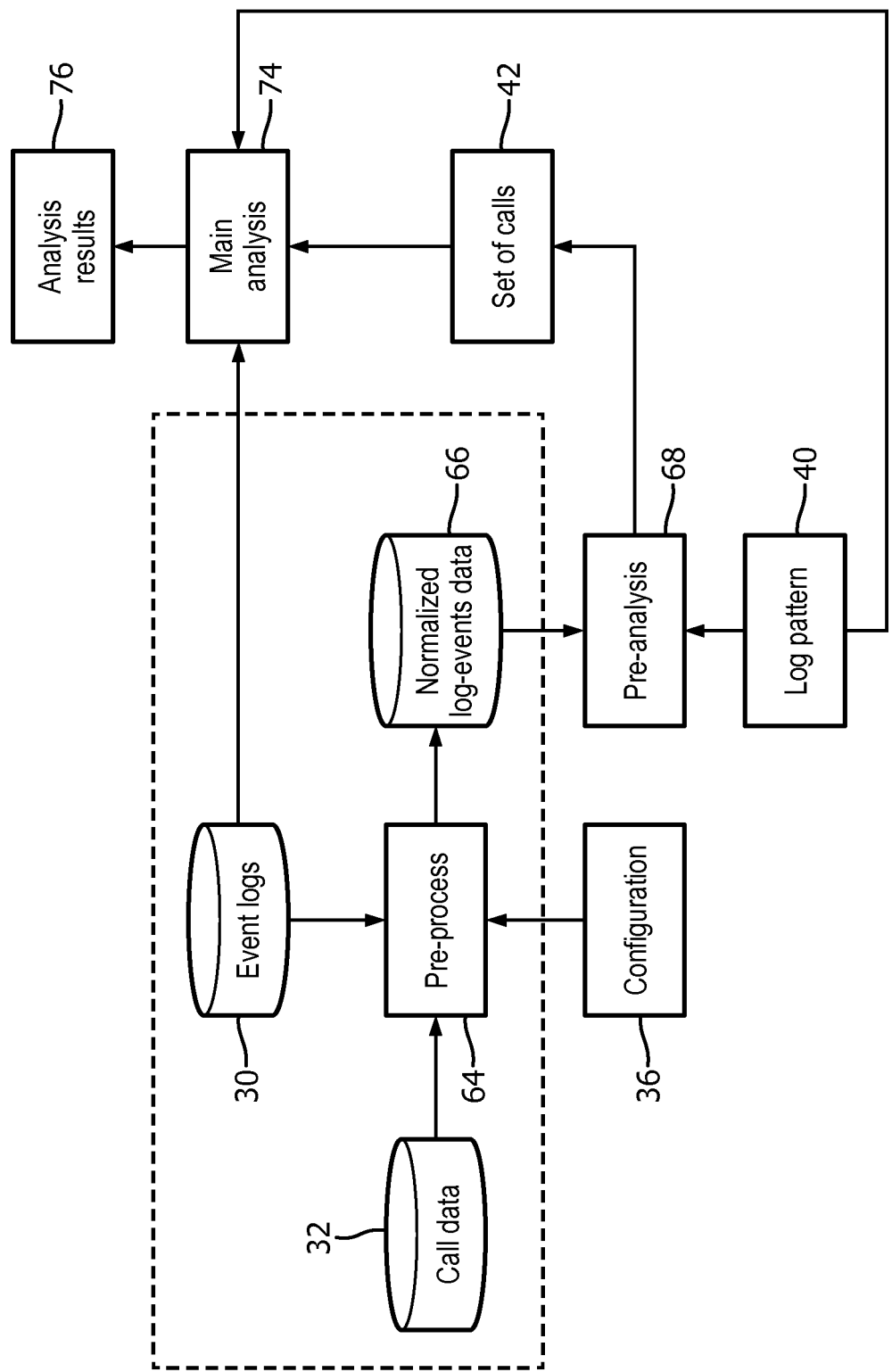
FIG. 2 diagrammatically illustrates an automated log pattern performance analysis method suitably performed by the device of FIG. 1.

With reference now to FIG. 2, an illustrative log analysis method suitably performed by the log pattern analysis device 10 of FIG. 1 is described. The method operates on log events data stored in the events log database 30 and on service calls stored in the service calls database 32. Preprocessing 64 is performed by the preprocessor 34 of FIG. 1 in accord with the configuration data 36 to produce normalized log events data 66. Pre-analysis 68 of the log pattern 40 under analysis is performed by the pre-analyzer 38 of FIG. 1 in order to generate the test set of service calls 42. A main analysis 74 is performed by the main analyzer 44 of FIG. 1 so as to generate analysis results 76, e.g. the hit service calls 46 and root cause(s) 48 identified in the hit service calls 46, and optionally additional result information such as the log events that match the log pattern 40 under analysis optionally with surrounding log events for context.

Based on a given configuration, the preprocessing 64 generates a list of normalized log-events data 66 and, for each normalized log event Î, a list of identifiers for service calls for which an associated log event l normalizes to Î. The normalized log-events data 66 is processed in the pre-analysis 68 that, given the log pattern 40 under analysis, determines the test set of service calls 42. These are next used by the main analysis 74 which, for each service call of the test set of service calls 42, retrieves the subset of log events occurring within the service call time frame of the call time of the service call and analyzes the given log pattern 40, based on this data, to calculate whether the log pattern 40 has a hit for this service call. These form the basis for the results 76 of the main analysis. The normalization step (i.e. preprocessing 64) employs normalization rules of the configuration data 36 to replace dates, times, integers, IP addresses, temperature values, etc., in attributes or fields of a log event, e.g. textual parts like the description and additional info, by constant strings, thus effectively mapping potentially many different log events onto one normalized log event. For example, a decimal integer will be replaced by the string <xxx>. It is contemplated for the normalized content to be simply removed (or, equivalently, to be replaced by the empty string < >). The test set of service calls 42 is typically significantly smaller than the total number of calls for the given configuration. This results in considerable savings in computation and data transport. For example, instead of retrieving, for 10,000 service calls, which may have a week's worth of associated log event data (or more) from a single machine, generating, on average 90,000 log events for analysis, by way of the preprocessing 64 and pre-analysis 68 it may suffice to only do this for some 150 calls.

In the following, some additional aspects and/or embodiments and/or examples are discussed with reference to the illustrative log pattern analysis method of FIG. 2.

In one illustrative example, the configuration 36 includes a time frame of, typically one or more years in the past (although a shorter time frame, e.g. on the order of months or even weeks, is alternatively contemplated), a set of system codes and releases that identify which systems the preprocessing 64 will be done, and the definition of the service call time frame, e.g., one day or one week extending backward in time from the call time of the service call (again, longer or shorter service call time frames are contemplated, and moreover the service call time frame could extend partly forward in time past the call time of the service call).

For the given configuration 36, the preprocessing 64 creates, for each service call in the given time frame involving one of the identified systems, a list of all log events that were generated during the service call time frame by this system. These log events are normalized. Using this data, the list of normalized log events 66 is generated and, for each normalized log event Î, a list of all identifiers for service calls for which a log event l normalizes to Î. This preprocessing 64 only needs to be done once for a given configuration 36, after which the results 66 of this preprocessing 64 can be used repeatedly for many log patterns.

Figure 3:
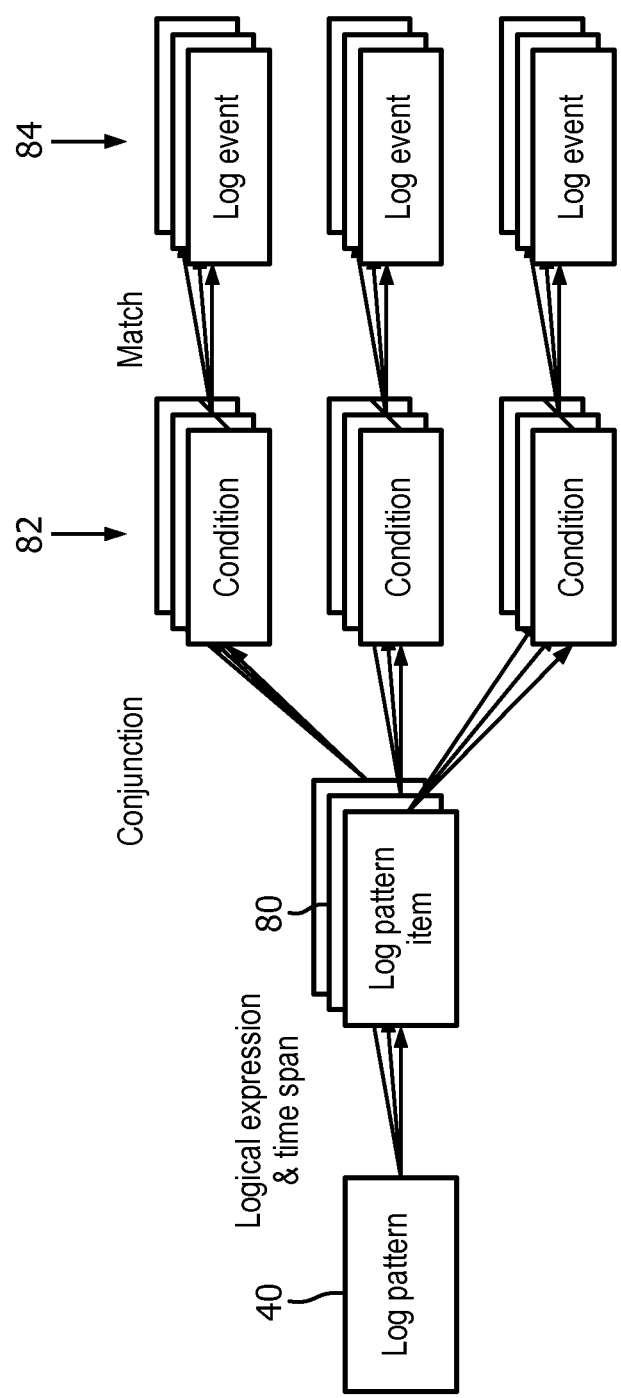
FIG. 3 diagrammatically illustrates a visual representation of decomposition of the structure of a log pattern into log events as described herein.

With continuing reference to FIG. 2 and with further reference to FIG. 3, in one illustrative example, the log pattern 40 comprises a logical expression, consisting of log pattern items 80, and a time span. For example, the logical expression could be A∧B∧¬(C∨D) in a time span of length at most t, where A, B, C, D are log pattern items, "∧" denotes a logical conjunction, "∨" denotes a logical disjunction, "¬" denotes a logical negation, and t denotes an amount of time. Each log pattern item 80 consists of a combination of conditions 82 on a single log event that, together, identify the set of log events 84 that each satisfy these conditions. This is illustrated visually in FIG. 3. These conditions 82 apply to the various attributes of which the log pattern 40 is composed. Examples are event id, event category, system mode, description, additional info. These conditions can be in terms of exact values, e.g., event id=0630000001 or system mode=normal operation, description=Generator exception occurred, but can also be in terms of regular expressions, e.g., additional info contains the regular expression POST (Clea|Poly-G2) LUC1 Passed. The pre-analysis 68 (see FIG. 2) normalizes the values of the description and additional info part of the conditions in this example. By contrast, the event id and event category are not normalized in this illustrative example. For each of the normalized log pattern items, normalized log events are identified that satisfy the normalized log pattern item, using the normalized log event data. By combining the call identifiers associated to each of these normalized log events, a set of call identifiers are obtained during which the log pattern item occurs. The preprocessing 64 can be applied to log patterns that are normalizeable. Let the normalized version of a log event l be denoted by l̂. Normalizeability of a log pattern means that each of its log pattern items that is not involved in a negation in conjunctive normal form (CNF), is normalizeable. Normalizeability of a log pattern item means that, if the log pattern item identifies a set S of log events, and the normalized version of this log pattern item identifies a set S' of normalized log events, then it holds that for all l∈S, we have l̂∈S'. In other words, a log pattern is normalizeable whenever the normalized version identifies a superset of its hits.

In general, a log pattern is normalizeable. Consider, the condition description=abc15 in a log pattern item. It identifies all log events that have description=abc15. In one normalization approach, normalization of the condition changes it to description=abc<xxx>. This normalized condition identifies all normalized log events that have description=abc<xxx>, the normalized version of the original description in the log event. Also for most regular expressions, this property holds. For example the regular expression (05AH|06AW) can be normalized to (<xxx>AH|<xxx>AW), so that an original log event containing 05AH will, once normalized, contain <xxx>AH. It will be appreciated that an original log event containing 02AH will also contain <xxx>AH, matching the normalized condition, so that normalization may generate more hits. As an aside, there are a few instances of regular expressions that are not normalizeable. For example, A {5}, which means five As in a row. Depending on the exact normalization procedure, normalization may change this to A{<xxx>}, which is not a valid regular expression, and may generate no match on any normalized log event. This can be detected, so that an exception can be thrown and the evaluation stops.

Now, two things are calculated in this example. First, by using the sets of calls associated to each of the normalized log pattern items in the log pattern, the logical expression of the log pattern can be evaluated, e.g. using Dijkstra's Shunting algorithm, to translate it to reverse Polish notation and performing a stack-based evaluation of this expression in reverse Polish notation. But, while doing this evaluation, each negation operator is evaluated to true, i.e., to all calls considered. The time span is also not taken into account. It can be shown that, in this way, a superset of all service calls is obtained in which the original log pattern has at least one hit. Including the time span in the main analysis 74 is suitably done with a window-based algorithm.

It will be appreciated that the disclosed preprocessing and pre-analysis provides savings in computational effort as well as in transport of data, e.g., over a network. In addition, the preprocessing and pre-analysis facilitates generation of log patterns of higher quality, which is expected to have a positive impact on the maintenance of medical systems, in particular in terms of reduced total cost of ownership and less unplanned downtime.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory storage medium storing:
   configuration data including at least a service call time frame and normalization rules for removing or replacing content; and
   instructions readable and executable by an electronic processor to perform a log pattern analysis method operating on medical imaging device log data including log events and further including service calls each having a call time wherein each service call is associated with a subset of log events occurring within the service call time frame of the call time of the service call, the log pattern analysis method comprising:
      performing preprocessing of the medical imaging device log data including generating normalized log events by removing or replacing content of the log events according to the normalization rules and linking each normalized log event with one or more service calls having associated log events matching the normalized log event;
      performing pre-analysis including identifying a test set of normalized log events that match a log pattern under analysis and a test set of service calls linked with the test set of normalized log events;
      analyzing the test set of service calls to identify hit service calls wherein each hit service call belongs to the test set of service calls and the log pattern under analysis has a hit for each hit service call; and
      controlling a display to present a log pattern report summarizing the hit service calls.

2. The non-transitory storage medium of claim 1 wherein performing the pre-analysis includes identifying the test set of normalized log events that match the log pattern under analysis using overinclusive matching in which removed or replaced content of the normalized log events is matched to corresponding normalized log pattern items using predefined normalized content matching rules.

3. The non-transitory storage medium of claim 1 wherein:
   the log pattern under analysis includes a first log pattern under analysis and a second log pattern under analysis,
   the preprocessing is performed once to generate the normalized log events; and
   the pre-analysis and the analyzing are performed a first time for the first log pattern under analysis and a second time for the second log pattern under analysis.

4. The non-transitory storage medium of claim 1 wherein:
the analyzing operation of the log pattern analysis method includes identifying one or more root causes identified by the hit service calls; and
the log pattern report summarizing the hit service calls contains information on the identified one or more root causes.

5. The non-transitory storage medium of claim 1 wherein at least a portion of the configuration data is hard coded into the instructions which are readable and executable to perform the log pattern analysis method.

6. The non-transitory storage medium of claim 1 wherein the non-transitory storage medium further stores instructions readable and executable by an electronic processor to perform a log pattern editing method including:
presenting a user interface via which the log pattern under analysis can be edited and the log pattern analysis method can be invoked to present the log pattern report summarizing the hit service calls for the edited log pattern under analysis.

7. The non-transitory storage medium of claim 6 wherein, via the user interface presented by the log pattern editing method, the edited log pattern under analysis can be stored as a deployed log pattern annotated with one or more root causes determined by the hit service calls.

8. The non-transitory storage medium of claim 7 further storing instructions readable and executable by an electronic processor to perform a diagnostic assistance method including:
applying the deployed log pattern to medical imaging device log data generated by a medical imaging device-under-service; and
conditional upon the deployed log pattern having at least one match in the medical imaging device log data generated by a medical imaging device-under-service, controlling a display to present the one or more root causes annotated to the deployed log pattern.

9. A medical imaging device diagnosis system comprising:
a non-transitory storage medium as set forth in claim 8;
a server computer operatively connected with the non-transitory storage medium to read and execute the instructions to perform the log pattern analysis method;
a diagnostic design computer operatively connected with the non-transitory storage medium to read and execute the instructions to perform the log pattern editing method; and
a field service engineer computer operatively connected with the non-transitory storage medium to read and execute the instructions to perform the diagnostic assistance method.

10. A medical imaging device diagnostic design system comprising:
a non-transitory storage medium as set forth in claim 1;
a server computer operatively connected with the non-transitory storage medium to read and execute the instructions to perform the log pattern analysis method; and
a diagnostic design computer operatively connected with the non-transitory storage medium to read and execute the instructions to perform the log pattern editing method.

11. A log pattern analysis device comprising:
an electronic processor; and
a non-transitory storage medium storing instructions readable and executable by the electronic processor to perform a log pattern analysis method operating on medical imaging device log data including log events and further including service calls each having a call time wherein each service call is associated with a subset of log events occurring within a service call time frame of the call time of the service call, the log pattern analysis method comprising:
performing preprocessing of the medical imaging device log data including generating normalized log events by removing or replacing content of the log events and linking each normalized log event with one or more service calls having associated log events matching the normalized log event;
performing pre-analysis including identifying a test set of normalized log events that match a log pattern under analysis and a test set of service calls linked with the test set of normalized log events; and
analyzing the test set of service calls to identify hit service calls wherein each hit service call belongs to the test set of service calls and the log pattern under analysis has a hit for each hit service call.

12. The log pattern analysis device of claim 11 wherein performing the pre-analysis includes identifying the test set of normalized log events that match the log pattern under analysis using overinclusive matching in which removed or replaced content of the normalized log events is matched to corresponding normalized log pattern items using predefined normalized content matching rules.

13. The log pattern analysis device of claim 11 wherein:
the log pattern under analysis includes a first log pattern under analysis and a second log pattern under analysis,
the preprocessing is performed once to generate the normalized log events; and
the pre-analysis and the analyzing are performed a first time for the first log pattern under analysis and a second time for the second log pattern under analysis.

14. A log pattern editing device comprising:
a log pattern analysis device as set forth in claim 11; and
a diagnostic design computer programmed to present a user interface via which a log pattern under analysis can be edited and via which the log pattern analysis device can be invoked and a log pattern report generated including at least one of a quantification of the hit service calls and one or more root causes identified by the hit service calls.

15. The log pattern editing device of claim 14 wherein the log pattern report includes a quantification of the hit service calls comprising at least one of a count of the hit service calls and a ratio of the count of the hit service calls to a count of service calls in the medical imaging device log data.

16. A medical imaging device diagnostic design system comprising:
a log pattern analysis device as set forth in claim 11;
a diagnostic design computer programmed to present a user interface via which a log pattern under analysis can be edited and via which the log pattern analysis device can be invoked and a log pattern report generated including at least one of a quantification of the hit service calls and one or more root causes identified by the hit service calls; and
a field service engineer computer programmed to apply a log pattern edited by the diagnostic design computer to medical imaging device log data generated by a medical imaging device-under-service and, conditional on the applied log pattern having at least one match in the medical imaging device log data, displaying one or more root causes associated with the applied log pattern on a display of the field service engineer computer.

17. A log pattern analysis method operating on medical imaging device log data including log events and further including service calls each having a call time wherein each service call is associated with a subset of log events occurring within a service call time frame of the call time of the service call, the log pattern analysis method comprising:
- removing or replacing content of the log events of the medical imaging device log data to generate normalized log events and linking each normalized log event with one or more service calls having associated log events matching the normalized log event;
- identifying a test set of normalized log events that match a log pattern under analysis and a test set of service calls linked with the test set of normalized log events; and
- analyzing the test set of service calls to identify hit service calls wherein each hit service call belongs to the test set of service calls and the log pattern under analysis has a hit for each hit service call;
- wherein the log pattern analysis method is performed by an electronic processor.

18. The log pattern analysis method of claim 17 wherein identifying the test set of normalized log events that match the log pattern under analysis includes matching removed or replaced content of the normalized log events to corresponding normalized log pattern items using predefined normalized content matching rules.

19. The log pattern analysis method of claim 17 further comprising:
- identifying one or more root causes determined by the hit service calls; and
- operating a display to present the identified one or more root causes.

20. The log pattern analysis method of claim 17 further comprising:
- computing at least one of a count of the hit service calls and a ratio of the count of the hit service calls to a count of service calls in the medical imaging device log data; and
- operating a display to present the computed count or ratio.

* * * * *